United States Patent [19]

Neh et al.

[11] Patent Number: 4,837,220

[45] Date of Patent: Jun. 6, 1989

[54] INSECTICIDAL 3-SUBSTITUTED 4-FLUOROPHENYL-1-(FLUOROALKOXY-PHENYLCARBAMOYL)-PYRAZOLINES

[75] Inventors: Harribert Neh; Ulrich Bühmann; Hartmut Joppien; David Giles, all of Berlin, Fed. Rep. of Germany

[73] Assignee: Schering Akt., Fed. Rep. of Germany

[21] Appl. No.: 119,191

[22] Filed: Nov. 10, 1987

[30] Foreign Application Priority Data

Nov. 11, 1986 [DE] Fed. Rep. of Germany ....... 3638631

[51] Int. Cl.$^4$ .................. A61K 31/345; C07D 231/06
[52] U.S. Cl. ........................................ 514/403; 548/379
[58] Field of Search ........................ 548/379; 514/403

[56] References Cited

U.S. PATENT DOCUMENTS 4,572,914  2/1986  Van Hes et al. ................... 514/403

Primary Examiner—Mary C. Lee
Assistant Examiner—J. Richter
Attorney, Agent, or Firm—Ostrolenk, Faber, Gerb & Soffen

[57] ABSTRACT

Pyrazolines of general formula I

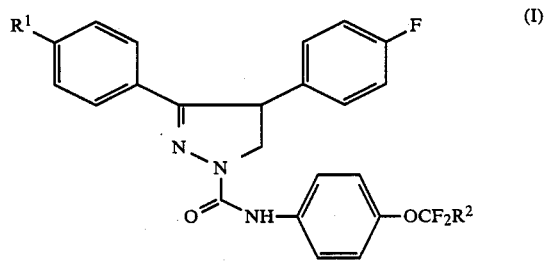

wherein $R^1$ and $R^2$ are the same or different and are hydrogen or fluorine, are described, as well as processes for their preparation and their use as insecticides and acaricides.

15 Claims, No Drawings

INSECTICIDAL 3-SUBSTITUTED 4-FLUOROPHENYL-1-(FLUOROALKOXY-PHENYLCARBAMOYL)-PYRAZOLINES

The present invention relates to new pyrazoline derivatives, their preparation and their use as pesticides.

Pyrazolines with insecticidal activity are already known (see for example DOS Nos. 23 04 584 and 25 29 689 as well as EP Nos. 21 506 and 113 213). This invention relates to pyrazoline derivatives having insecticidal and acaricidal activity.

In EP No. 21506, there are claimed pyrazoline compounds of formula

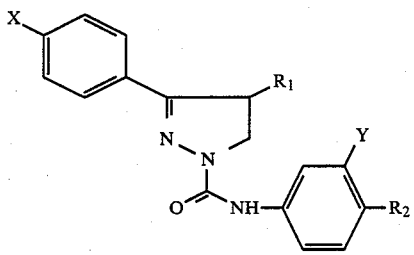

wherein $R_1$ is, inter alia, a phenyl group or a halogen substituted phenyl group, $R_2$ is, inter alia, a halogenoalkoxy having 1 to 6 carbon atoms and X and Y are hydrogen or halogen. Of the compounds where $R_1$ is a phenyl group, two are described in which $R_1$ is a free phenyl group or a p-chlorophenyl group, $R_2$ is trifluoromethoxy and X is chloro. All published compounds, in which $R_1$ is a halo substituted phenyl group, have only X=chloro as the substituent on the phenyl group in the 3-position.

The object of the present invention is to provide pyrazoline derivatives that have a greater activity and better selectivity.

It has now been found that pyrazolines of general formula I

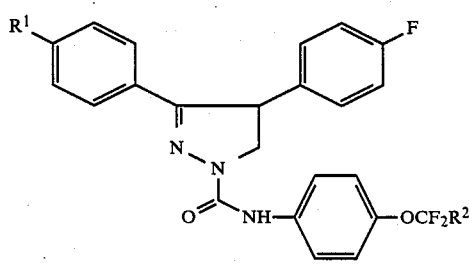

wherein
$R^1$ and $R^2$ are the same or different and are hydrogen or fluorine, have improved activity in comparison with known pyrazolines.

In many cases they also have reduced mammalian toxicity in comparison with known compounds of closely related structures.

The invention includes all isomeric forms and mixtures of these.

The compound of the invention of formula I can be prepared by reacting a pyrazoline of general formula II

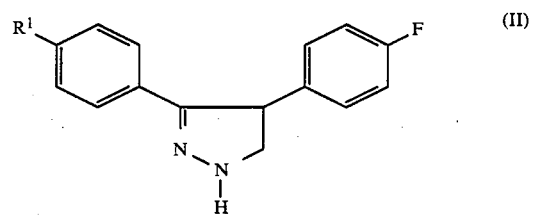

either
(A) with an isocyanate of formula III

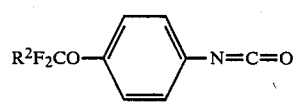

optionally using a solvent, or
(B) with the reaction product from trichloromethyl chloroformate and an aniline of formula IV

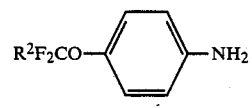

optionally using a solvent, in which $R^2$ has the meaning given in formula I.

Suitable solvents are liquids which are inert to the reactants such as aliphatic, alicyclic and aromatic hydrocarbons, which can be optionally chlorinated, e.g. hexane, cyclohexane, petroleum ether, benzene, toluene, xylene, dichloroomethane, chloroform, carbon tetrachloride, 1,2-dichloroethane, trichloroethylene and chlorobenzene; ethers, such as diethyl ether, methyl ethyl ether, diisopropyl ether, dibutyl ether, dioxane and tetrahyrofuran; nitriles, such as acetonitrile, propionitrile and benzonitrile; esters, such as ethyl acetate and amyl acetate; amides, such as dimethylformamide, N-methylpyrrolidone or hexamethylphosphoric acid triamide, as well as sulphones and sulphoxides, such as dimethyl sulphoxide and sulpholane.

The reaction variants (A) and (B) can be carried out over a wide temperature range. Generally, the temperature is between −20° C. and 100° C., preferably at room temperature.

The reaction can be carried out at normal atmospheric pressure but it can also be carried out at higher or reduced pressures.

The compounds of the invention prepared by the above processes can be isolated from the reaction mixture in conventional manner, for example by distillation of the solvent at normal or reduced pressure, by precipitation with water or by extraction. A higher degree of purity can as a general rule be achieved by column chromatography or by recrystallisation.

The pyrazoline derivatives of the invention are colourless and odourless and in most cases, crystalline compounds. They are highly insoluble in water and toluene, slightly more soluble in ethyl acetate and highly soluble in dimethylformamide.

The pyrazolines of formula II used as starting materials of are either known or can be prepared according to known processes.

The isocyanates of formula III used as starting material in reaction variant A are either known or can be prepared according to known processes.

The anilines of formula IV used as starting material in reaction variant B are either known or can be prepared according to known processes.

The compounds of the invention have insecticidal and acaricidal activity and are particularly useful in combating a variety of economically important insects, and acarids including animal ectoparasites. Examples include Lepidoptera, such as *Plutella xylostella, Spodoptera littoralis, Heliothis armigera* and *Pieris brassicae;* Diptera, such as *Musca domestica, Ceratitis capitata, Erioischia brassicae, Lucilia sericata* and *Aedes aegypti;* Homoptera, including aphids such as *Megoura viciae* and *Nilaparvata lugens;* Coleoptera, such as *Phaedon cochleariae, Anthonomus grandis* and *Epilachna varivestis* and corn rootworms (Diabrotica spp., e.g., *Diabrotica undecimpunctata*); Orthoptera, such as cockroaches e.g. *Blattella germanica;* Hymenoptera, such as ants e.g. *Monomorium pharaonis;* mange mites, e.g. Sarcoptes spp.; ticks, such as *Boophilus microplus* and lice, such as *Damalinia bovis* and *Linognathus vituli;* as well as spider mites such as *Tetranychus urticae* and *Panonychus ulmi.*

The compounds of the invention are distinguished by a surprisingly high level of activity against important pest species, especially pest insects, which represents a valuable improvement in the art.

The compounds according to the invention can be used at a concentration of 0.0005 to 5%, preferably from 0.001 to 1%, calculated as gram active material per 100 ml of the composition.

The compounds of the invention can be used either alone or in mixture with each other or another insecticide. Optionally other plant protection or pesticidal compositions, such as for example insecticides, acaricides or fungicides can be added depending on the desired result.

An improvement in the intensity and speed of action can be obtained, for example, by addition of suitable adjuvants, such as organic solvents, wetting agents and oils. Such additives may allow a decrease in the dose.

Suitable mixture partners may include phospholipids, e.g. phosphatidylcholine, hydrated phosphatidylcholines, phosphatidylethanolamine, N-acyl-phosphatidylethanolamines, phosphatidylinositol, phosphatidylserine, lysolecithin or phosphatidylglycerol.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example, water aliphatic and aromatic hydrocarbons such as benzene, toluene, xylene, cyclohexanone, isophorone, dimethyl sulphoxide, dimethylformamide, other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The level of the respective active ingredients in the various preparations can vary over wide ranges. For example the composition may contain about 10 to 90 percent by weight of active ingredient, about 90 to 10 percent liquid or dry carriers, as well as optionally up to 20 percent by weight of surfactant.

The composition can be applied in conventional manner, for example using water as the carrier in spray amounts of about 100 to 3000 liters/ha. Application in so called low volume or ultra-low-volume proceeses is possible as well as by so-called microgranules.

Formulations can be prepared, for example, from the following ingredients.

A WETTABLE POWDER
20 percent by weight active ingredient
35 percent by weight bentonite
8 percent by weight calcium lignosulphonate
2 percent by weight of the sodium salt of N-methyl-N-oleyltaurine
35 percent by weight silicic acid B PASTE
45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water C EMULSIFIABLE CONCENTRATE
20 percent by weight active ingredient
75 percent by weight isophorone
5 percent by weight of an emulsifier mixture of calcium phenylsulphonate and fatty alcohol polyglycol ether The following examples illustrate the preparation of compounds according to the invention.

EXAMPLE 1

N-(4-Difluoromethoxyphenyl]-3,4-bis-(4-fluorophenyl)-4,5-dihydropyrazole-1-carboxamide 9.85 g (0.038 mol) 3,4-bis-(4-fluorophenyl)-4,5-dihydropyrazole in 80 ml dichloromethane was treated with 7.03 g (0.038 mol) 4-difluoromethoxyphenyl isocyanate, with stirring at room temperature and stirred for an hour at room temperature. The reaction mixture was filtered through silica gel and the filtrate was concentrated. The residue was treated with 100 ml diisopropyl ether. The precipitated crystals were separated and dried in vacuo (100 Torr).

Yield: 14.7 g (87% of theory).
M.p.: 144° C.

In a similar manner the following compounds were obtained, in which the substitutents $R^1$ and $R^2$ have the meanings given in formula I.

| Example No. | $R^1$ | $R^2$ | m.P. (°C.) |
|---|---|---|---|
| 2 | F | F | 135 |
| 3 | H | F | 146 |
| 4 | H | H | 140 |

The following Examples illustrate the biological activity of the compounds of the invention.

Test Example A

Activity in curative treatment of broad beans (*Vicia fabae* L.) against black bean aphids (*Aphis fabae* scop.).

In a heated greenhouse, broad bean (*Vicia fabae*) seedlings (one plant per pot) were grown until about 6 cm high. The plants were then treated with cultures of black bean aphids (*Aphis fabae*). After the plants had been colonised with 100 to 200 adults, they were sprayed until dripping wet with aqueous preparations of each active material containing 0.1% of active material and put in a greenhouse at about 24° C. After 2 days, the amount of dead aphids was determined. The activity was calculated according to Abbott in comparison with several untreated control pots.

With the compounds of the invention of Examples 1 and 4 an activity of more than 75% was achieved.

Test Example B

Activity in prophylactic treatment of leaves against brown rice-hoppers (*Niliparvata lugens Stal*).

In a heated greenhouse, rice seedlings (about 15 per pot) were grown until formation of the third leaf and then sprayed until dripping wet with an aqueous preparation containing 0.1% of active material. After drying the sprayed leaves, a transparent cylinder was placed over each pot. 30 Adult brown rice-hoppers (*Niliparvata lugens*) were introduced into each pot. After 2 days at 26° C. in the greenhouse, the amount of dead hoppers was determined. The activity was calculated according to Abbott in comparison with several untreated control pots.

For the compounds of Examples 1-4 the activity reached 75-100%.

Test Example C

Activity against larvae of diamond-backed moth (*Plutella xylostella*).

Formulations of compounds of the invention were made up with an active ingredient content of 0.0064%. The desired concentration was achieved by diluting solutions in acetone or emulsifiable concentrates with water. Cabbage leaves (*Brassica oleracea gongylodes*), placed in polystyrene petri dishes, were sprayed with these preparations (4 mg spray/cm$^2$). After the sprayed surface had dried, 10 young larvae of the diamond-backed moth (*Plutella xylostella*) were placed in each petri dish and thereby exposed to the treated food in the closed dishes for two days. Feeding with untreated cabbage leaves then followed for a further three days. The % mortality of the larvae after five days indicated the level of activity.

Compounds according to Examples 1-4 showed an activity of 80-100%.

Test Example D

Activity against larvae (L 2) of the cotton army worm (*Spodoptera littoralis*).

Formulations of compounds of the invention were made up with an active ingredient content of 0.0064%. The desired concentration was achieved by diluting solutions in acetone or emulsifiable concentrates with water. Leaflet pairs of beans (*Vicia fabae*) as well as 10 larvae (L 2) of the cotton army worm (*Spodoptera littoralis*) per experiment were sprayed with 4 mg spray/cm$^2$ of these preparations in polystyrene petri dishes. The closed petri dishes were left in the laboratory under extended daylight conditions for two days. Feeding with untreated bean leaves then followed for a further three days. The % mortality of the larvae after 5 days indicated the level of activity.

Compounds according to Examples 1-4 showed an activity of 80-100%.

Test Example E

Contact activity against larvae (L 2) of the cotton bollworm (*Heliothis viriscens*).

Formulations of compounds of the invention were made up with an active ingredient content of 0.0064%. The desired concentration was achieved by diluting solutions in acetone or emulsifiable concentrates with water. The inner surface of petri dishes were sprayed with 4 mg spray/cm$^2$ of these preparations. After drying the spray coating, 5 larvae of the cotton bollworm (*Heliothis viriscens* per petri dish were exposed to the spray coating for 24 hours. After this the larvae were placed in untreated petri dishes and fed with a non toxic artificial diet for another 4 days. The tests were carried out in the laboratory under extended daylight conditions. The % mortality of the larvae after 5 days indicated the level of activity.

Compounds according to Examples 1-4 showed an activity of 80-100%.

Test Example F

Soil insecticide activity against eggs/larvae of the corn rootworm (*Diabrotica undecimpunctata*).

Formulations of compounds of the invention were made up with an active ingredient content of 0.0064%. The desired concentration was achieved by diluting solutions in acetone or emulsifiable concentrates with water. 20 ml of this preparation was poured into each plastic flower pot (66×66×82 mm) each of which was filled with 200 ml earth and ca. 100 eggs of the corn rootworm (*Diabrotica undecimpunctata*) as well as 2 grains of corn (*Zea mays*) at a depth of ca 1 cm of soil. The pots were left in the glasshouse under extended daylight conditions and at 24°-26° C. for 14 days. The criterion for judging the activity was the emergence of maize plants in untreated pots with and without eggs within 14 days.

It was shown that compounds according to Examples 1-4 gave undisturbed plant growth.

Test Example G

Insecticidal activity against sheep blowfly (*Lucilia sericata*).

1 ml Aliquots of an acetone solution containing test compound at various concentrations were applied to cotton wool dental rolls 1 cm×2 cm, contained in glass vials (2 cm diameter×5 cm long). After drying, the treated materials were then impregnated with 1 ml of nutrient solution, infested with first instar larvae of sheep blowfly (*Lucilia sericata*), closed by a cotton wool plug and held at 25° C. for 24 hours.

At a concentration of 0.1 ppm compounds of Examples 1-3 gave 100% mortality. This mortality was reached at 3 ppm with the compound of Example 4.

For the purposes of comparison, the compounds of EP 21506 having the closest structure were also tested. These are compound 2: N-(4-trifluoromethoxyphenyl]-3-(4-chlorophenyl)-4-phenyl-4,5-dihydropyrazole-1-carboxamide. and compound 10: N-(4-trifluoromethoxyphenyl]-3-3,4-bis-(4-chlorophenyl)-4,5-dihydropyrazole-1-carboxamide. At 0.1 ppm, compound 2 gave 70% mortality and compound 10 gave 20% mortality.

We claim:

1. Pyrazolines of formula I

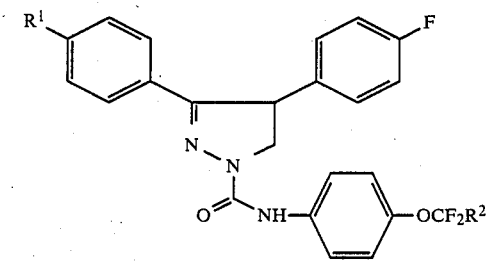

wherein

R¹ and R² are the same or different and are hydrogen or fluorine.

2. Pyrazoline according to claim 1 in which R¹ and R² are both fluorine.

3. Pyrazoline according to claim 1 in which R¹ and R² are both hydrogen.

4. Pyrazoline according to claim 1 in which R¹ is hydrogen and R² is fluorine.

5. Pyrazoline according to claim 1 in which R¹ is fluorine and R² is hydrogen.

6. An insecticidal or acaricidal composition which comprises a compound claimed in claim 1, in admixture with an agriculturally acceptable diluent or carrier.

7. A method for combating insects or acarids which comprises applying to the insect, acarid or their locus an effective amount of a compound claimed in claim 1.

8. An insecticidal or acaricidal composition which comprises a compound claimed in claim 4, in admixture with an agriculturally acceptable diluent or carrier.

9. An insecticidal or acaricidal composition which comprises a compound claimed in claim 3, in admixture with an agriculturally acceptable diluent or carrier.

10. An insecticidal or acaricidal composition which comprises a compound claimed in claim 4, in admixture with an agriculturally acceptable diluent or carrier.

11. An insecticidal or acaricidal composition which comprises a compound claimed in claim 5, in admixture with an agriculturally acceptable diluent or carrier.

12. A method for combatting insects or acarids which comprises applying to the insect, acarid or their locus an effective amount of a compound claimed in claim 2.

13. A method for combatting insects or acarids which comprises applying to the insect, acarid or their locus an effective amount of a compound claimed in claim 3.

14. A method for combatting insects or acarids which comprises applying to the insect, acarid or their locus an effective amount of a compound claimed in claim 4.

15. A method for combatting insects or acarids which comprises applying to the insect, acarid or their locus an effective amount of a compound claimed in claim 5.

* * * * *